United States Patent [19]

Kasafírek et al.

[11] Patent Number: 5,318,973
[45] Date of Patent: Jun. 7, 1994

[54] NEUROPROTECTIVE COMPOSITION FOR PREVENTING OR TREATING OF CENTRAL NERVOUS SYSTEM IMPAIRMENT

[75] Inventors: Evžen Kasafírek; Ivan Krejči; Zdeněk Hliňák; Martin Valchář; Karel Dobrovský; Antonín Šturc; Milan Pešák; Arnošt Pospíšil; all of Prague, Czechoslovakia

[73] Assignee: Vyzkumny Ustav Pro Farmacii a Biochemii

[21] Appl. No.: 71,980

[22] Filed: Jun. 7, 1993

[51] Int. Cl.$^5$ ............................................. A61K 31/505
[52] U.S. Cl. ..................................... 514/269
[58] Field of Search ........................... 514/269

[56] References Cited

PUBLICATIONS

M. Poctová et al, "Fluorimetrie ve Farmaceutické", *Ceskoslovenska Farmacie*, Rocnik XXXVIII, Cislo 6, 198, pp. 245–247 (English Language Abstract).
Chem. Abst.–109–156289f (1988).
Chem. Abst.–111 180–847y (1989).

*Primary Examiner*—Zohreh Fay
*Attorney, Agent, or Firm*—Burns, Doane, Swecker & Mathis

[57] ABSTRACT

The present application is directed to a method of treating central nervous system disorders originating as a consequence of head injury or brain ischemia. The method comprises administering an effective amount of cyclo-(L-alanyl-1-amino-1-cyclopentane carbonyl) to treat a central nervous system disorder in a mammalian organism in need of such treatment. The administration may be conducted either orally or parenterally.

6 Claims, No Drawings

NEUROPROTECTIVE COMPOSITION FOR PREVENTING OR TREATING OF CENTRAL NERVOUS SYSTEM IMPAIRMENT

FIELD OF THE INVENTION

The invention relates to a neuroprotective composition for preventing or treating central nervous system impairment, e.g. originating as a consequence of head injury or of brain ischemia. The subject composition comprises as the physiologically active component a specific spirocyclic dipeptide, cyclo-(1-alanyl-1-amino-1-cyclopentanecarbonyl, and is designated for administration by oral or parenteral route; it has only slight toxicity, is well tolerated and acts beneficially even at low dosage level.

DESCRIPTION OF PRIOR ART

It has been well established that several types of insults like hypoxia, ischemia or head injury cause lesions and impair functioning of the mammalian brain. The central nervous system is also susceptible to the toxic effect of several exogenous substances with different modes of action. On the other hand drugs are available, that could protect the brain from irreversible impairment resulting from the aforementioned insults. For example, Flunarizine (Janssen) (E)-1-{bis(p-fluorophenyl)methyl}-4-cinnamyl-piperazine, has been shown to protect the brain from morphological and functional impairment in several experimental models of cerebral ischemia (e.g. Life Sciences 48, 1881–1893, 1991).

In the search for neuroprotective agents it has been found that a specific spirocyclic dipeptide, cyclo-(alanyl-1-amino-1-cyclopentanecarbonyl), possesses properties indicating therapeutic potential in treating the aforementioned brain impairments. This compound has been shown to improve performance of laboratory animals in tests used to assess the effects on learning and memory and exhibited antiamnesic action (CS 231 227). The compound also inhibited the development of tolerance to the cataleptic effect after repeated administration of neuroleptics as well as the development of dopamine receptors supersensitivity in the rat striatum. This experimental evidence indicates a possible use of the compound either in drug-induced dyskinesias or idiopathic Parkinson's disease.

This spirocyclic dipeptide also stimulated the growth of the diploid cells of human embryonic lungs. This finding led to the use of the compound for treatment of gastric ulcers (CS 260 899; U.S. Pat. No. 5,182,285). Further experimental findings revealed beneficial effects of the dipeptide on the impairment of central nervous system induced in laboratory animals by acute intoxication with sodium nitrite. Behavioral alteration resulting from the toxic effect of sodium nitrite was ammeliorated, if the compound was administered to the animals for 5 days.

SUMMARY OF THE INVENTION

Said cell-protective composition comprises, as a physiologically active component, a specific spirocyclic dipeptide, cyclo-(-1-alanyl-1-amino-1-cyclopentanecarbonyl) of formula I:

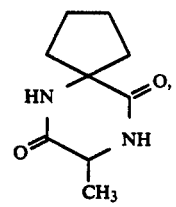

This specific spirocyclic dipeptide is optionally combined with a physiologically inert vehicle (carrier substrate) which enables either oral or parenteral administration.

The observations of the protecting and/or healing properties of the aforenamed compound in animal models of cerebral damage show that it has neuroprotective properties that can be exploited in the treatment of central nervous system disorders originating from brain insults of various origin. The following experimental methods and results support this conclusion.

1. Focal Freezing Cortical Lesions—Morphological Study

Focal freezing injury was produced in male mice (strain NMRI) by applying a metal probe cooled to $-75°$ C. to the exposed skull of ether-anaesthetized animals. After 3 or 14 days the animals were sacrificed and the brains were histologically examined. The extent of the lesion was measured and a semiquantitative estimation performed.

Experiment 1

Compound I was administered in a dose 10 mg/kg orally, two times a day, starting 4 days before the injury and continuing for another 3 or 14 days. The size of the lesion was clearly smaller at the 3rd day after the insult in the treated animals. At the 14 days interval there was a reduction in the size of the lesions in both treated a control animals, however, the lesions in the treated animals were again smaller (Tab. 1, upper part)

Experiment 2

In this experimental setup the treatment with compound I started with an intravenous injection (10 mg/kg) immediately after the injury and went on with oral administration of the same dose twice a day for 3 or 14 days. Again there was a clear shift to the smaller size of lesions in the treated animals at both intervals (Tab.1, lower part).

2. Impairment of the Central Nervous System with the Neurotoxin Trimethyltin—Behavioral Study Acute intoxication with trimethyltin (TMT) causes neural death in the brain and is reflected in neurochemical changes affecting various neurotransmitter systems. Also behavior is altered; TMT administration produces a syndrome characterized by aggression, tremor and hyperactivity (Pharmacol. Rev. 37,365,1985, Neurotoxicology 9, 481,1988). A detailed analysis of the exploratory activity of the rat (strain Wistar/Hannover) disclosed a marked increase of the "floor-sniffing" behavior and a significant decrease of "resting" posture for several weeks after TMT administration.

TABLE 1

| GROUP | DAY | N | SIZE OF THE LESION[1] % | | | |
|---|---|---|---|---|---|---|
| | | | 0–25 | 26–50 | 51–75 | 76–100 |
| Exp. 1 | | | | | | |
| Comp 1 | 3 | 15 | 4 | 8 | 2 | 1[2] |
| Control | 3 | 17 | 0 | 1 | 3 | 13 |
| Comp 1 | 14 | 14 | 13 | 1 | 0 | 0 |
| Control | 14 | 15 | 2 | 13 | 0 | 0 |
| Exp. 2 | | | | | | |
| Comp 1 | 3 | 5 | 0 | 4 | 1 | 0 |
| Control | 3 | 6 | 0 | 0 | 2 | 4 |
| Comp 1 | 14 | 5 | 4 | 1 | 0 | 0 |
| Control | 14 | 5 | 0 | 5 | 0 | 0 |

[1] size of the lesion is expressed in percent of the maximal lesion reaching the structures of corpus callosum
[2] FIGS. in the columns under the percentage ranges are numbers of animals The potential neuroprotective effect of the compound I was examined using a protective-curative dose regime.

Experiment 1

The spirocyclic dipeptide was administered daily in a dose of 5 mg/kg orally for 1 week before and for 2 weeks after a single dose of TMT (8 mg/kg s.c.). Animals were tested at day 15 and 23 after TMT injection. During the 1st testing neither the time spent in sniffing nor in resting differed between the animals having received TMT only and those treated with TMT+compound I. However, during the 2nd testing both the sniffing and resting levels of TMT+compound I treated rats corresponded to the levels of the controls (Table 2).

Experiment 2

To determine the therapeutic effect the compound of formula I was administered twice daily (5 mg/kg orally) one day before, on the same day, and one day after the injection of TMT (8 mg/kg subcutaneously). Thereafter compound I was administered in the drinking water (10 mg/kg daily) for another 22 or 26 days. Behavioral testing was performed at day 27. Accordingly, the animals treated with the compound I for 22 days were not under the influence of the drug when tested. The "floor-sniffing" behavior increased in TMT impaired animals was lowered in animals treated with both dosage schemes of compound I (Table 2).

In addition to the behavioral testing, the examination of neurotransmitter levels and of their metabolites were performed in the brain of the animals. In the group treated for 22 days the rats were killed 10 days after the last administration of compound I. In the group treated for 26 days, the animals had the same dose of compound I in the drinking water for another 5 days, i.e. they were killed 31 days after the TMT intoxication. Compound I partly restored the altered levels of homovanillic acid (HVA) in the striatum and hypothalamus, of 5-HT in the cortex and of 5-hydroxyindole acetic acid (5-HIAA) in the hypothalamus (Table 3, 4, 5).

TABLE 2

| Group | N | "Floor-sniffing" Testing Day | | "Resting"[1] Testing Day | |
|---|---|---|---|---|---|
| | | 15 | 23 | 15 | 23 |
| Exp. 1 | | | | | |
| Control | 9 | 98.1 | 63.9 | 5.1 | 58.9 |
| TMT | 9 | 143.7 | 132.6 | 1.1 | 12.8 |
| TMT + Comp I | 9 | 120.8 | 76.7 | 0.1 | 82.3 |
| Comp I | 9 | 98.2 | 39.4 | 33.4 | 145.4 |
| Exp. 2 | | 27 | | 27 | |
| Control | 12 | 48.3 | | 16.2 | |
| TMT | 11 | 134.9 | | 7.2 | |
| TMT + Comp I/22 | 12 | 83.9 | | 2.6 | |
| TMT + Comp I/26 | 12 | 74.4 | | 5.7 | |
| Comp I | 12 | 41.4 | | 27.8 | |

[1] total time in sec

TABLE 3

| | STRIATUM | | | |
|---|---|---|---|---|
| | DA (ng/g) | N | HVA (ng/g) | N |
| Control | 7023 | 9 | 313 | 5 |
| Comp I | 6279 | 9 | 222 | 5 |
| TMT | 7662 | 9 | 184[1] | 6 |
| TMT + Comp I/22 | 6366[2] | 9 | 289 | 4 |
| TMT + Comp I/31 | 6131[1,2] | 10 | 277 | 4 |

[1] significant difference (p 0.05) compared to control group
[2] significant difference compared to TMT-group

TABLE 4

| | CEREBRAL CORTEX | | | |
|---|---|---|---|---|
| | NA[2] (ng/g) | N | 5-HT (ng/g) | N |
| Control | 321 | 11 | 282 | 5 |
| Comp I | 394 | 9 | 291 | 6 |
| TMT | 420 | 9 | 209[1] | 5 |
| TMT + Comp I/22 | 343 | 9 | 247 | 6 |
| TMT + Comp I/31 | 314 | 6 | 237 | 4 |

[1] significant difference (p 0.05) compared to control group
[2] noradrenalin

TABLE 5

| | HYPOTHALAMUS | | | | | |
|---|---|---|---|---|---|---|
| | NA (ng/g) | N | 5-HT | N | 5-HIAA | N |
| Control | 578 | 10 | 714 | 10 | 1264 | 10 |
| Comp I | 695[1] | 8 | 593[1] | 12 | 1317 | 10 |
| TMT | 671 | 9 | 608[1] | 9 | 1598[1] | 9 |
| TMT + Comp I/22 | 413[1,2] | 8 | 563[1] | 10 | 1329[2] | 10 |
| TMT + Comp I/31 | 548[2] | 9 | 607[1] | 10 | 1426 | 10 |

[1] significant difference (p 0.05) compared to control group
[1] significant difference (p 0.05) compared to TMT-group In a similar experimental paradigm Flunarizine was administered at a daily dose of 5 mg/kg orally for 7 days before and 2 weeks after TMT (8 mg/kg s.c.). The behavior of animals was examined on the 15th and 23rd day after TMT injection. Flunarizine restored the altered behaviors at both intervals (Tab. 6).

The results of these studies show an improvement of both behavioral and neurochemical consequences of TMT neurotoxic effects by the compound of formula I, which are comparable with the protective effects of flunarizine.

TABLE 6

| | | "Floor-sniffing" Testing Day | | "Resting "[1] Testing Day | |
|---|---|---|---|---|---|
| GROUP | N | 15 | 23 | 15 | 23 |
| Control | 9 | 98.1 | 63.9 | 5.1 | 58.9 |
| TMT | 9 | 143.7 | 132.6 | 1.1 | 12.8 |
| TMT + Flun | 9 | 115.8 | 76.7 | 5.4 | 82.3 |
| Flunarizine | 9 | 93.6 | 40.0 | 20.3 | 142.2 |

[1] total time in sec

The cyclo-(L-alanyl-1-amino-1-cyclopentanecarbonyl) may be administered in an effective amount to treat central nervous system disorders, specifically those originating as a consequence of head injury and ischemia. The specific dosage range is preferably between 0.1 mg/kg per day.

The subject compound of formula I can be administered, in accordance with the origin and severity of the impairment, either parenterally (by injection or intravenous infusion) or orally, by ingestion of any convenient oral dispensing form (tablets, coated tablets, capsules, suspensions and the like). Usual dosage involves 1 to 2 tablets of 50 mg daily. To insure rapid onset of the effect or upon impaired consciousness of the patient parenteral route of administration is preferable. In such a case a 2 to 5 mg dose in the form of, e.g., 2 to 5 ml injections can administered t.i.d. After achieving a desired introductory improvement the parenteral therapy is conveniently improved by the aforementioned oral treatment. Due to substantial nontoxicity and good tolerance of the subject agent, oral therapy can be continued for several weeks or months.

DETAILED EXAMPLES

Further particulars of the subject composition and preferable procedures for its formulation are illustrated by the subsequent nonlimitative examples.

EXAMPLE 1

Injections

| Compound of formula I | 0.100 g |
|---|---|
| Mannitol | 4.800 g |
| Water for injections | ad 100.0 ml |

Compound I and mannitol are successively dissolved in water for injections and the solution is sterilized by filtration and aseptically filled into ampoules of 5 ml volume. The obtained injections, when stored in a cold and dark environment, are stable for at least 1 year.

EXAMPLE 2

Injections

| Compound of formula I | 1.00 g |
|---|---|
| $KH_2PO_4$ | 0.86 g |
| $Na_2HPO_4.12H_2O$ | 0.14 g |
| NaCl | 8.20 g |
| Water for injections | ad 1000.00 ml |

Phosphates, sodium chloride and compound I are successively dissolved in water for injections. The solution is sterilized by filtration and aseptically filled into ampoules of 2 ml volume. The obtained injections, when stored in a cold (5°–15° C.) and dark environment, are stable for at least 1 year.

EXAMPLE 3

Tablets (Direct Tableting)

| Compound of formula I | 10.00 g |
|---|---|
| Sorbitol | 44.00 g |
| Microcrystalline cellulose | 90.00 g |
| Polyvinylpyrrolidone | 4.50 g |
| Magnesium stearate | 1.50 g |

Compound I is intensively mixed with microcrystalline cellulose and successively to the mixture sorbitol, polyvinylpyrrolidone and magnesium stearate are added. From the obtained powdery mixture tablet cores are prepared of 7 mm diameter and 150 mg weight. The resulting cores are optionally coated with a polymeric film-forming material, e.g. hydroxpropylmethylcellulose, or a sugar solution.

EXAMPLE 4

Tablets (via Granulation)

| Compound of formula I | 10.00 g |
|---|---|
| Lactose | 116.40 g |
| Sodium carboxymethyl starch | 32.00 g |
| Magnesium stearate | 1.60 g |

Compound I is successively mixed with lactose and a portion (14 g) of sodium carboxymethyl starch and homogenized. The homogenizate is granulated with the use of 10 g of carboxymethyl starch in the form of 10% of hydrogel. The so formed wet granulation is dried at a temperature of 50° C., the dry material is mixed with magnesium stearate and 8 g of sodium carboxymethyl starch. The mixture is homogenized and tableted to prepare tablet cores of 7 mm diameter and 160 mg weight.

We claim:

1. A method for the neuroprotective treatment of central nervous system disorders originating as a consequence of head injury and ischemia, which comprises administering to a mammalian organism a physiologically active compound, cyclo-(L-alanyl-1-amino-1-cyclopentane carbonyl), of formula I:

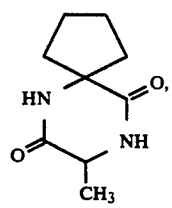

(I)

2. A method of treating central nervous disorders originating as a consequence of head injury or brain ischemia in a mammal, said method comprising administering an effective amount of cyclo-(L-alanyl-1-amino-1-cyclopentane carbonyl) to treat a central nervous system disorder in a mammalian organism in need of such treatment.

3. The method as recited in claim 2 wherein said cyclo-(L-alanyl-1-amino-1-cyclopentane carbonyl) is orally administered.

4. The method as recited in claim 3 wherein said cyclo-(L-alanyl-1-amino-1-cyclopentane carbonyl) is orally administered at a dose of one or two 50 mg tablets daily.

5. The method as recited in claim 2 wherein said cyclo-(L-alanyl-1-amino-1-cyclopentane carbonyl) is parenterally administered.

6. The method as recited in claim 5 wherein 2 to 5 mg of said cyclo-(L-alanyl-1-amino-1-cyclopentane carbonyl) is parenterally administered three times a day.

* * * * *